United States Patent
Mori et al.

(10) Patent No.: US 9,068,934 B2
(45) Date of Patent: Jun. 30, 2015

(54) GAS SENSOR PROCESSING APPARATUS

(71) Applicant: NGK SPARK PLUG CO., LTD., Nagoya-shi, Aichi (JP)

(72) Inventors: Kentaro Mori, Nagoya (JP); Soichi Kawaguchi, Inazawa (JP); Ryosuke Ichida, Komaki (JP); Yoshinori Hibino, Kasugai (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 219 days.

(21) Appl. No.: 13/739,543

(22) Filed: Jan. 11, 2013

(65) Prior Publication Data
US 2013/0180853 A1   Jul. 18, 2013

(30) Foreign Application Priority Data

Jan. 13, 2012 (JP) ................. 2012-004568

(51) Int. Cl.
*G01N 27/409* (2006.01)
*F02D 41/14* (2006.01)
*G01N 27/406* (2006.01)

(52) U.S. Cl.
CPC .......... *G01N 27/409* (2013.01); *F02D 41/1455* (2013.01); *F02D 41/1494* (2013.01); *F02D 41/1495* (2013.01); *G01N 27/4065* (2013.01)

(58) Field of Classification Search
CPC ..... G01N 27/04; G01N 27/409; G01N 27/41; G01N 33/007; F01N 11/007
USPC ........................ 73/23.31, 23.32; 204/421–429
See application file for complete search history.

(56) References Cited

U.S. PATENT DOCUMENTS

| | | | |
|---|---|---|---|
| 5,852,228 A | 12/1998 | Yamashita et al. | |
| 5,974,857 A | 11/1999 | Yamashita et al. | |
| 6,099,717 A | 8/2000 | Yamada et al. | |
| 2010/0108540 A1* | 5/2010 | Kato et al. | 205/781 |
| 2011/0172876 A1* | 7/2011 | Kimoto et al. | 701/34 |

FOREIGN PATENT DOCUMENTS

| | | | |
|---|---|---|---|
| JP | 5-209852 A | 8/1993 | |
| JP | 10-26599 A | 1/1998 | |
| JP | 10-142191 A | 5/1998 | |

(Continued)

OTHER PUBLICATIONS

Machine translation JP 2011-086074, run Oct. 1, 2014.*

(Continued)

*Primary Examiner* — Jennifer Dieterle
(74) *Attorney, Agent, or Firm* — Sughrue Mion, PLLC

(57) ABSTRACT

A gas sensor processing apparatus (1) which includes voltage shift means (11, 19, S1071) for shifting a detection element voltage VE produced between electrodes (3P, 3N) of a detection element (3) from a pre-shift voltage VE1 to a post-shift voltage VE2; recovery means (11, 19, S1072) for returning the detection element voltage VE from the post-shift voltage VE2 to the pre-shift voltage VE1 after the end of a voltage shift period TS in which the voltage VE is shifted by the voltage shift means; and deterioration index detection means S106-S107 for detecting a deterioration index ID representing the degree of deterioration of the detection element (3) on the basis of a voltage change in the recovery period TK in which the voltage VE is recovered by the recovery means.

7 Claims, 6 Drawing Sheets

(56) References Cited

FOREIGN PATENT DOCUMENTS

| | | |
|---|---|---|
| JP | 10-185857 A | 7/1998 |
| JP | 2004-28676 A | 1/2004 |
| JP | 2011-86074 A | 4/2011 |

OTHER PUBLICATIONS

Japanese Office Action mailed Mar. 18, 2014 issued in relevant Japanese Patent Application No. 2012-004568.

* cited by examiner

GAS SENSOR PROCESSING APPARATUS

BACKGROUND OF THE INVENTION

1. Field of the Invention

The present invention relates to a gas sensor processing apparatus for processing the output of a gas sensor which detects the concentration of a specific gas.

2. Description of the Related Art

Conventionally, a gas sensor has been used which is disposed in an exhaust pipe of an internal combustion engine of a vehicle and is adapted to detect the concentration of a specific gas contained in exhaust gas for the purpose of, for example, controlling the air-fuel ratio of fuel mixture supplied to the internal combustion engine. For example, an oxygen sensor for detecting the concentration of oxygen and an NOx sensor for detecting the concentration of nitrogen oxide (NOx) are known. In these gas sensors, a solid electrolyte body mainly made of zirconia (zirconium oxide) is commonly used as a detection element. The solid electrolyte body exhibits good oxygen ion conductivity at a high temperature of about 600° C. or higher (activated state). Also, by utilizing a phenomenon that the impedance (internal resistance) of the detection element changes with the element temperature, the temperature of the detection element is detected. Further, in order to maintain the detection element at a predetermined temperature within a range in which the detection element becomes active, the supply of electric current to a separately provided heater is feedback-controlled such that the element impedance becomes equal to a target impedance.

[Patent Document 1] Japanese Patent Application Laid-Open (kokai) No H10-26599

PROBLEMS TO BE SOLVED BY THE INVENTION

The impedance (internal resistance) of a detection element of such a gas sensor increases gradually when the gas sensor deteriorates due to use thereof and other causes. Therefore, the impedance (internal resistance) of a deteriorated detection element measured at a certain temperature becomes higher than that measured at the same temperature before the detection element has deteriorated. Accordingly, accurate detection of the temperature of the detection element is difficult. Also, when the above-mentioned feedback control for the heater is performed, in order to cause the element impedance to approach the target impedance, the supply of electric current is controlled such that the element impedance decreases; namely, such that the element temperature increases. Therefore, a problem arises in that the element temperature increases as the element impedance increases, and the temperature increase accelerates deterioration of the detection element.

An oxygen concentration detection apparatus which can solve the above problems is disclosed, for example, in Patent Document 1. The subject oxygen concentration detection apparatus includes deterioration determination means for determining a deteriorated state in which the impedance of the detection element has increased; and target impedance change means for increasing a target impedance when the detection element is determined to be in a deteriorated state. Heater-supplied-power comparison means for comparing the electric power supplied to a heater and a predetermined value for determination is disclosed as a specific example of the deterioration determination means.

However, when the oxygen concentration detection apparatus is used, the gas sensor must be configured to include a heater as an essential component. In addition, the oxygen concentration detection apparatus has encountered difficulty in accurately detecting the degree of deterioration of the detection element. This is because a change in the electric power supplied to the heater is not determined only by an increase in the element impedance caused by deterioration of the detection element, but is also apt to be influenced by various external disturbances.

SUMMARY OF THE INVENTION

The present invention has been accomplished in order to solve the above problems, and an object thereof is to provide a gas sensor processing apparatus which can accurately detect the degree of deterioration of a detection element of a gas sensor.

The above object of the invention has been achieved by providing (1) a gas sensor processing apparatus for processing an output of a gas sensor including a detection element which is formed of a solid electrolyte body, which has a pair of electrodes, and which detects the concentration of a specific gas. The gas sensor processing apparatus comprises voltage shift means for shifting a detection element voltage produced between the electrodes of the detection element from a pre-shift voltage to a post-shift voltage different from the pre-shift voltage; recovery means for returning the detection element voltage from the post-shift voltage to the pre-shift voltage through self-discharge by an internal capacitor of the detection element after the end of a voltage shift period in which the detection element voltage is shifted by the voltage shift means; and deterioration index detection means for detecting a deterioration index representing the degree of deterioration of the detection element on the basis of a change in the detection element voltage in a recovery period in which the detection element voltage is returned to the pre-shift voltage by the recovery means.

The detection element formed of a solid electrolyte body exhibits oxygen ion conductivity at a temperature of about 400° C. or higher. When the detection element in this state is represented by an equivalent circuit, the detection element can be considered to have a series circuit between the electrodes thereof, the series circuit including a cell (concentration cell) which generates an electromotive force in accordance with the concentration of a specific gas such as oxygen and an internal impedance element whose impedance decreases as the element temperature increases. The internal impedance element can be considered to be composed of a pure resistor (internal resistor) and an internal capacitor connected in parallel.

In view of the above, in the present gas sensor processing apparatus, the detection element voltage produced between the electrodes of the detection element is shifted from a pre-shift voltage to a post-shift voltage by the voltage shift means. The detection element voltage produced between the electrodes of the detection element is forcedly changed, for example, by externally applying a voltage between the electrodes of the detection element, the voltage being greater than the electromotive force generated by the detection element. As a result, due to the voltage superimposed (added) by the voltage shift, a current flows through the internal resistor of the detection element, whereby a voltage drop is produced. If the electromotive force of the detection element is assumed to be constant, the voltage superimposed by the voltage shift corresponds to the voltage drop produced by the internal resistor of the detection element. In the voltage shift period in which the voltage shift is performed, due to the superimposed voltage, a current flows through the internal resistor, and a charge is accumulated in the internal capacitor of the detection element.

Further, after the end of the voltage shift period, the detection element voltage is returned from the post-shift voltage to the pre-shift voltage. The deterioration index detection means detects a deterioration index, which represents the degree of deterioration of the detection element, on the basis of a voltage change occurring in the recovery period in which the detection element voltage returns from the post-shift voltage toward the pre-shift voltage. In the recovery period, the charge accumulated in the internal capacitor of the detection element due to the voltage superimposed by the voltage shift self-discharges through the internal resistor of the detection element. As a result, the voltage between the electrodes of the detection element decreases exponentially at a rate corresponding to a time constant generally determined by the internal resistance and the internal capacitance of the detection element so that a voltage change from the post-shift voltage back to the pre-shift voltage is produced.

When the detection element deteriorates, the impedance of the detection element tends to increase, and the internal resistance thereof at the same temperature (at a certain temperature) also increases. In addition, the internal capacitance also changes. Therefore, the way (trend) of the above-described exponential voltage change differs (varies) depending on the degree of deterioration. Also, this voltage change is hardly affected by external disturbances, and is generally determined by the impedance of the detection element. Accordingly, the present gas sensor processing apparatus, which detects the deterioration index on the basis of this voltage change, can accurately detect the degree of deterioration of the detection element of the gas sensor. In other words, in the present invention, the deterioration determination is performed by making use of a characteristic in which the discharge of the charge at the time of self-discharge (the above-described voltage change) is affected by the internal resistance and the internal capacitance.

Notably, examples of the method of shifting the detection element voltage from the pre-shift voltage to the post-shift voltage different from the pre-shift voltage include a method of applying a constant voltage between the electrodes of the detection element via a switching element such as a transistor or an FET; a method of applying a constant voltage between the electrodes of the detection element via a switching element and an external resistor disposed between the switching element and the detection element so that a resistor-divided voltage is applied; and a method of supplying a constant current to the detection element by a constant current source so that a voltage drop is produced across the internal resistor.

Also, an example method of returning the detection element voltage from the post-shift voltage to the pre-shift voltage through self-discharge of the detection element is to stop (cut off) the external current flowing between the electrodes of the detection element or the external voltage applied to the electrodes.

Also, an example method of detecting the deterioration index, which represents the degree of deterioration of the detection element, on the basis of a voltage change produced in the recovery period is measuring the detection element voltage at a predetermined timing within the voltage shift period and the detection element voltage at a predetermined timing within the recovering period following the voltage shift period, and calculating the difference between these voltages as the deterioration index. Another example method of detecting the deterioration index is measuring the detection element voltages at predetermined two timings within the recovering period, and calculating the difference between these voltages as the deterioration index. Still another example method of detecting the deterioration index is periodically measuring the detection element voltage produced between the electrodes of the detection element within the recovery period, and detecting, as the deterioration index, the time constant of an exponential function which approximates a curve which represents the changing detection element voltage. Preferably, the deterioration index is detected under a consistent or constant condition, for example, when the internal resistance of the detection element is equal to a predetermined value.

In a preferred embodiment (2) of the above-described gas sensor processing apparatus (1), the gas sensor includes a heater for heating the detection element; and the gas sensor processing apparatus further comprises first internal resistance detection means for detecting a first internal resistance which is an internal resistance of the detection element when the detection element detects the concentration of the gas; first heater energization control means for feedback-controlling the supply of electric current to the heater such that the first internal resistance becomes equal to a target resistance; and target resistance correction means for correcting the target resistance in accordance with the deterioration index detected by the deterioration index detection means.

In this gas sensor processing apparatus, since the supply of electric current to the heater can be properly feedback-controlled by changing the target resistance in accordance with the state of deterioration of the detection element, the element temperature can be maintained at a proper activation temperature. In addition, acceleration of the deterioration by an increase in the element temperature can be prevented.

In another preferred embodiment (3) of the above-described gas sensor processing apparatus (1) or (2) above, the gas sensor processing apparatus further comprises resistance index detection means for detecting a resistance index before the deterioration index detection means detects the deterioration index, the resistance index being the internal resistance of the detection element or an internal voltage proceeds from the internal resistance, wherein the deterioration index detection means detects the deterioration index when the resistance index is equal to a predetermined detection permission value.

In this gas sensor processing apparatus, the deterioration index is detected in a period in which the resistance index becomes equal to the detection permission value. By virtue of this configuration, the deterioration index can be detected under a constant condition, whereby the deterioration index can be detected accurately.

In yet another preferred embodiment (4) of the above-described gas sensor processing apparatus (3), the gas sensor includes a heater for heating the detection element; and the gas sensor processing apparatus further comprises second heater energization control means for feedback-controlling the supply of electric current to the heater such that the resistance index detected by the resistance index detection means becomes equal to the detection permission value.

In this gas sensor processing apparatus, the deterioration index can be detected reliably at a timing at which the resistance index becomes equal to the detection permission value.

Preferably, the above-described gas sensor processing apparatus is configured such that the deterioration index detection means detects, as the deterioration index, a 1-2 voltage difference, which is the difference between a first voltage, which is the detection element voltage at a first detection timing within the voltage shift period, and a second voltage, which is the detection element voltage at a second detection timing within the recovery period following the voltage shift period.

In this gas sensor processing apparatus, the 1-2 voltage difference, which serves as the deterioration index, can be easily obtained by merely measuring two voltages; i.e., the first voltage at the first detection timing within the voltage shift period and the second voltage at the second detection timing within the recovery period following the voltage shift period.

Notably, the first detection timing may be any timing within the voltage shift period. Preferably, the first detection timing is a timing within a later portion of the voltage shift period in which the detection element voltage approaches the post-shift voltage, more preferably, a timing in an end portion (at the end) of the voltage shift period in which the detection element voltage becomes equal to the post-shift voltage.

Also, the second detection timing may be any timing within the recovery period. Preferably, the second detection timing is a timing within the recovery period before the detection element voltage converges to the pre-shift voltage. More preferably, the second detection timing is determined such that the greatest variation arises in the detected detection element voltage among different degrees of deterioration.

Preferably, the above-described gas sensor processing apparatus is configured such that the resistance index detection means and the voltage shift means share a circuit which shifts the detection element voltage of the detection element from the pre-shift voltage to the post-shift voltage.

In this gas sensor processing apparatus, it is unnecessary to prepare separate circuits for the resistance index detection means and the voltage shift means. Therefore, the gas sensor processing apparatus can be made inexpensive and compact.

Preferably, the above-described gas sensor processing apparatus is configured such that the deterioration index detection means detects the deterioration index in a period in which the internal resistance of the detection element is greater than a first internal resistance which is the internal resistance at the time when the detection element detects the concentration of the gas.

When the concentration of a specific gas is detected, the detection element is heated to a sufficiently high temperature and is activated, and its internal resistance is controlled to a low value (e.g., 100 Ω or less). Therefore, if an attempt is made to detect the deterioration index of the detection element in such a state by the deterioration index detection means, difficulty is encountered in accurately detecting the deterioration index. This is because the voltage change produced in the recovery period is small, and the rate of voltage change is high.

In contrast, according to this gas sensor processing apparatus, the change in the detection element voltage produced in the recovery period is large and not abrupt. Therefore, the deterioration index can be detected accurately.

DESCRIPTION OF REFERENCE NUMERALS AND SYMBOLS

Figure 1:
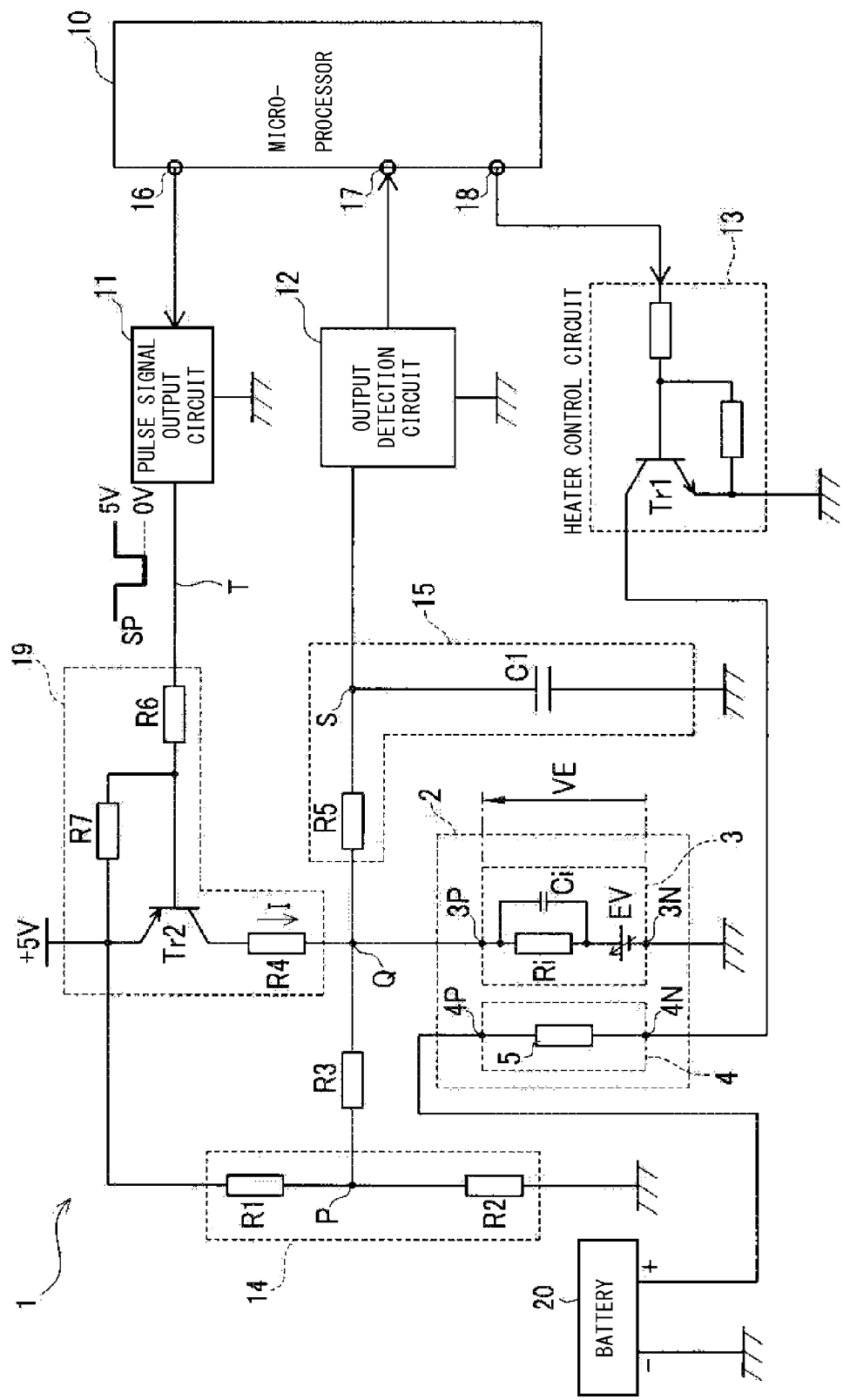
FIG. 1 is an explanatory diagram schematically showing a configuration including the circuit of an oxygen sensor control apparatus according to an embodiment of the invention.

Reference numerals used to identify various features in the drawings include the following.

1: oxygen sensor control circuit (gas sensor processing apparatus)
2: oxygen sensor (gas sensor)
3: detection element
3P, 3N: electrode
4: heater
EV: electromotive force (of an oxygen concentration cell)
Ri: internal resistance
Ci: internal capacitance
10: microprocessor
11: pulse signal output circuit (resistance index detection means, voltage shift means, recovery means)
12: output detection circuit (resistance index detection means)
13: heater control circuit (first heater energization control means, second heater energization control means)
15: low-pass filter circuit (resistance index detection means)
19: voltage shift circuit (resistance index detection means, voltage shift means, recovery means)
20: battery
VE: detection element voltage
VE1: pre-shift voltage
VE2: post-shift voltage
TS: voltage shift period
TK: recovery period
ID: deterioration index
Ri1: first internal resistance
RT: target resistance
RTh: corrected target resistance
RU: second target resistance (detection permission value)
IR: resistance index
t1: first detection timing
t2: second detection timing
V1: first voltage
V2: second voltage
V1-2: 1-2 voltage difference (deterioration index)
S2: first internal resistance detection means
S4: target resistance correction means
S5: first heater energization control means
S101 to S103: resistance index detection means
S104: second heater energization control means
S106 to S107: deterioration index detection means
S1071: voltage shift means
S1072: recovery means Detailed Description Of The Preferred Embodiments An embodiment of the present invention will now be described with reference to the drawings. However, the present invention should not be construed as being limited thereto.

FIG. 1 is a diagram schematically showing the configuration of an oxygen sensor control apparatus 1, which is a gas sensor processing apparatus. The oxygen sensor control apparatus 1 is mounted on a vehicle (not shown) having an unillustrated engine. The oxygen sensor control apparatus is used in conjunction with an oxygen sensor 2 so as to control the same, and detects the concentration of oxygen contained in exhaust gas from the engine.

The oxygen sensor 2 includes a detection element 3 in which a pair of electrodes 3P and 3N are formed on an oxygen-ion-conductive solid electrolyte body mainly made of zirconia; and a heater 4 for heating the detection element 3. More specifically, one electrode 3N, which is formed on the outer circumferential surface of the detection element 3 composed of the solid electrolyte body having the shape of a cylindrical tube with a bottom, is exposed to the exhaust gas. The other electrode 3P, which is formed on the inner circumferential surface of the detection element 3, is exposed to a reference gas (atmosphere). The heater 4 having a barlike shape is inserted into the inner space of the detection element 3 having a bottomed-tubular shape, whereby the oxygen sensor 2 is formed. When the detection element 3 composed of the solid electrolyte body is heated by the heater 4 to an activation temperature higher than 600° C. at which the detection element 3 becomes activated, the detection element 3 exhibits a satisfactory oxygen-ion conductivity and is able to detect the concentration of oxygen. The supply of electric current to the heater 4 of the oxygen sensor 2 is controlled by the oxygen sensor control apparatus 1 such that the detection element 3 maintains a predetermined temperature within a temperature range in which the detection element 3 becomes activated (hereinafter, this range is also referred to as an "activation temperature range").

The heater 4 includes a heat generation resistor 5 mainly made of tungsten or platinum, and terminals 4P and 4N connected to the heat generation resistor 5. One terminal 4P of the heater 4 is connected to the positive electrode of a battery 20. The negative electrode of the battery 20 is connected to a reference potential, which is the chassis GND of the vehicle (hereinafter referred to as "GND"). The other terminal 4N of the heater 4 is connected to the collector output of an NPN-type transistor Tr1 (a switching element) of a heater control circuit 13 via an unillustrated current limit resistor. The emitter of the transistor Tr1 is connected to GND. The base of the transistor Tr1 is connected to a PWM (pulse-width-modulation) output port 18 of a microprocessor 10. The heater control circuit 13 supplies electric current to the heater 4 by PWM control, whereby the detection element 3 is heated. When the detection element 3 is maintained at the predetermined temperature within the activation temperature range, the duty ratio of the PWM control is determined by PID (proportional-integral-derivative) control or PI (proportional-integral) control performed by the microprocessor 10. Notably, the switching element which constitutes the heater control circuit 13 is not limited to the transistor Tr1, and the heater control circuit 13 may be formed using an FET or the like. Notably, an unillustrated power supply circuit produces, from the battery 20, a +5 V supply for use in powering the oxygen sensor control apparatus 1 and a VCC supply (not shown) for powering the microprocessor 10.

The detection element 3 has an internal resistor having an internal resistance Ri, which decreases as the temperature of the solid electrolyte body increases. A predetermined correlation is known to exist between the internal resistance Ri and the temperature of the detection element 3. Therefore, the element temperature can be maintained at a predetermined temperature by controlling the internal resistance Ri such that it coincides with a target resistance.

The detection element 3 composed of the solid electrolyte body exhibits oxygen ion conductivity at about 400° C. or higher. Thus, the detection element 3 functions as an oxygen concentration cell due to a difference in oxygen concentration between the electrodes 3N and 3P, and generates an electromotive force EV corresponding to the oxygen concentration difference. Therefore, as shown in FIG. 1, the equivalent circuit of the detection element 3 is considered to have a series circuit which is located between the electrodes 3P and 3N and which includes a cell (oxygen concentration cell) generating the electromotive force EV and an internal impedance element. Notably, the internal impedance element is considered to be formed not only by an internal resistor (pure resistor) having an internal resistance Ri but also by an internal capacitor having a capacitance Ci connected in parallel to the internal resistor.

As described above, the solid electrolyte body constituting the detection element 3 has a characteristic such that the internal resistance Ri decreases as the temperature of the solid electrolyte body increases. However, in a portion of a non-active period, in which portion the temperature of the solid electrolyte body is low, the internal resistance Ri is high, which substantially insulates the electrodes 3P and 3N of the detection element 3 from each other. The internal resistance Ri decreases as the temperature of the solid electrolyte body increases, and exhibits a low value when the detection element 3 becomes active (active period). As the temperature of the solid electrolyte body increases, the detection element 3 begins to produce between the electrodes 3P and 3N an electromotive force EV corresponding to the oxygen concentration difference. Although the electromotive force EV in the active period changes depending on the element temperature, the electromotive force EV becomes about 900 mV when the air-fuel ratio of exhaust gas is on the rich side, and becomes about 50 mV when the air-fuel ratio of exhaust gas is on the lean side. The electromotive force EV sharply changes in the vicinity of a point at which the air-fuel ratio becomes equal to the theoretical air-fuel ratio between the rich side and the lean side ($\lambda$=1).

Returning to the description of the oxygen sensor control circuit 1 (see FIG. 1), a bias circuit 14 is provided which is composed of a series circuit including a resistor R1 and a resistor R2 and which divides the +5 V power supply by the resistor R1 and the resistor R2. In the present embodiment, R1 is set to 100 k$\Omega$, and R2 is set to 10 k$\Omega$ so that the potential at a node P produced as a result of division of the +5 V power supply by the resistor R1 and the resistor R2 becomes about 450 mV. The potential at the node P is selected such that it assumes an intermediate value between the above-described electromotive force of about 900 mV at the time when the air-fuel ratio is on the rich side and the above-described electromotive force of about 50 mV at the time when the air-fuel ratio is on the lean side. Through a resistor R3 (specifically, R3=10 k$\Omega$) which is a current limiting resistor, the node P is connected to the electrode 3P of the detection element 3 at a node Q. The other electrode 3N of the detection element 3 is connected to the GND.

The node Q is connected to the +5V power supply via a resistor R4 (specifically, R4=8.25 k$\Omega$) and a PNP-type transistor Tr2 which serves as a switching element. Notably, the switching element is not limited to the transistor Tr2, and may be an FET or the like. The node Q is also connected to a low-pass filter circuit 15 for removing noise which is composed of a resistor R5 and a capacitor C1 (specifically, R5=10 k$\Omega$, C1=0.033 µF). A node S, which is the output of the low-pass filter circuit 15, is connected to an output detection circuit 12. The output detection circuit 12 includes an unillustrated sample-and-hold circuit, and its output is connected to an A/D input port 17 of the microprocessor 10.

The emitter of the transistor Tr2 is connected to the +5 V power supply line, and the collector of the transistor Tr2 is connected to the resistor R4. A resistor R7 (base-emitter resistor) and a resistor R6 (base input resistor) are connected to the base of the transistor Tr2. The resistors R6 and R7, the transistor Tr2, and the resistor R4 constitute a voltage shift circuit 19. A pulse signal output circuit 11 is connected to a node T, which is one end of the resistor R6 of the voltage shift circuit 19. The pulse signal output circuit 11 is connected to an I/O output port 16 of the microprocessor 10, and an output from the I/O output port 16 is supplied through the pulse signal output circuit 11 to the node T as a pulse signal SP. The pulse signal SP is a negative-logic pulse signal having a rectangular waveform. In an ordinary state, the voltage of the pulse signal SP is maintained at +5 V, which is the same as the emitter potential of the transistor Tr2, so as to turn off the transistor Tr2 of the voltage shift circuit 19. Only in periods in which the transistor Tr2 is to be turned on, the voltage of the pulse signal SP temporarily becomes 0 V, and returns to +5 V. The pulse signal output circuit 11, which outputs this pulse signal SP, and the voltage shift circuit 19 perform the voltage shift described below.

Specifically, the pulse signal output circuit 11 buffers the output of the I/O output port 16 of the microprocessor 10 with or without inverting the polarity thereof, and converts the level of the output voltage from that of the VCC power of the microprocessor 10 to +5 V. The pulse signal output circuit 11 is formed by a buffer IC for level conversion, a transistor, etc. In the present embodiment, the pulse signal output circuit 11 is an inverted-type buffer circuit. Therefore, when the output of the I/O output port 16 is at the L level, the potential at the node T (the output of the pulse signal output circuit 11) becomes +5 V, and, when the output of the I/O output port 16 is at the H level, the potential at the node T (the output of the pulse signal output circuit 11) becomes 0 V.

First, the operations of these circuits will be considered for the case where the transistor Tr2 of the voltage shift circuit 19 is off. When the transistor Tr2 is off, no current flows through the resistor R4. In a portion of a non-active period, in which portion the temperature of the solid electrolyte body is low, the detection element 3 does not generate the electromotive force EV (EV=0 V). Also, its internal resistance Ri is close to a value representing an insulating state, and is far larger than the resistance (10 kΩ) of the resistor R2. Therefore, no current flows through the detection element 3, and no current flows through the current limit resistor R3. Therefore, when the temperature of the solid electrolyte body is low, the potential at the node P becomes about 450 mV, which is determined by the voltage division by the resistor R1 and the resistor R2. The potentials at the nodes Q and S become the same as the potential at the node P, and about 450 mV is input to the output detection circuit 12. Meanwhile, in an active period in which the solid electrolyte body has a sufficiently high temperature (for example, when the temperature of the detection element 3 is about 700° C.), the internal resistance Ri of the detection element 3 becomes 100 Ω or smaller, and becomes far smaller than those of the resistor R2 and the resistor R3. In this active period, the detection element 3 generates an electromotive force EV (about 900 mV on the rich side, about 50 mV on the lean side). Since the internal resistance Ri is sufficiently small as described above, the potential at the node Q is hardly affected by the current flowing through the resistors R2 and R3. Therefore, the potential at the node Q becomes approximately equal to the electromotive force EV. The potential at the node Q is passed through the low-pass filter circuit 15, and is input to the output detection circuit 12 at the node S. Thus, the output detection circuit 12 can detect the electromotive force EV of the detection element 3.

Next, the case where the transistor Tr2 of the voltage shift circuit 19 is on will be considered. In the period in which the transistor Tr2 is off, as described above, no current flows through the resistor R4. Meanwhile, when the transistor Tr2 is turned on, a current I flows through the resistor R4. Since the internal resistance Ri of the detection element 3 is far smaller than those of the resistors R3 and R2 when the detection element 3 is active, most of the current I flows through the detection element 3. Accordingly, in a state in which the current flowing through the internal capacitor having a capacitance Ci described below has become almost zero after convergence, the current I has a magnitude obtained by dividing, by the sum of the resistance of the resistor R4 and the internal resistance Ri of the detection element 3 (series combined resistance), a value obtained by subtracting the electromotive force EV of the detection element 3 and the emitter-collector voltage (≅0 V) of the transistor Tr2 from the +5 V power supply (I≅(5−EV)/(R4+Ri)). Here, a case is considered where the difference in oxygen concentration between the electrodes 3P and 3N does not change and the electromotive force EV is constant between the period in which the transistor Tr2 is off and the period in which the transistor Tr2 is on. In such a case, the detection element voltage VE in the period in which the transistor Tr2 is on is higher than the detection element voltage VE in the period in which the transistor Tr2 is off by an amount corresponding to a voltage drop (Ri×I) produced across the internal resistor (internal resistance Ri). Namely, as a result of the transistor Tr2 being turned on, a voltage shift occurs; i.e., the detection element voltage VE is shifted from a pre-shift voltage VE1 (=EV) to a post-shift voltage VE2 (=EV+Ri×I).

The difference (VE2−VE1) between the post-shift voltage VE2 and the pre-shift voltage VE1 is used as the shift voltage VS. Since the pre-shift voltage VE1 is equal to the electromotive force EV generated by the detection element 3 when the transistor Tr2 is off, the shift voltage VS serves as an internal voltage Vi corresponding to the voltage drop produced as a result of the flow of the current through the internal resistor (internal resistance Ri). This internal voltage Vi is represented by Vi=Ri×(5−EV)/(R4+Ri). Accordingly, the magnitude of the shift voltage VS; i.e., the internal voltage Vi, can be determined by detecting the pre-shift voltage VE1 (=EV) and the post-shift voltage VE2 (=VE1+VS=EV+Vi) by the output detection circuit 12. Also, the internal resistance Ri can be obtained from the ratio of the internal resistance Ri to the resistance of the resistor R4.

Figure 2:
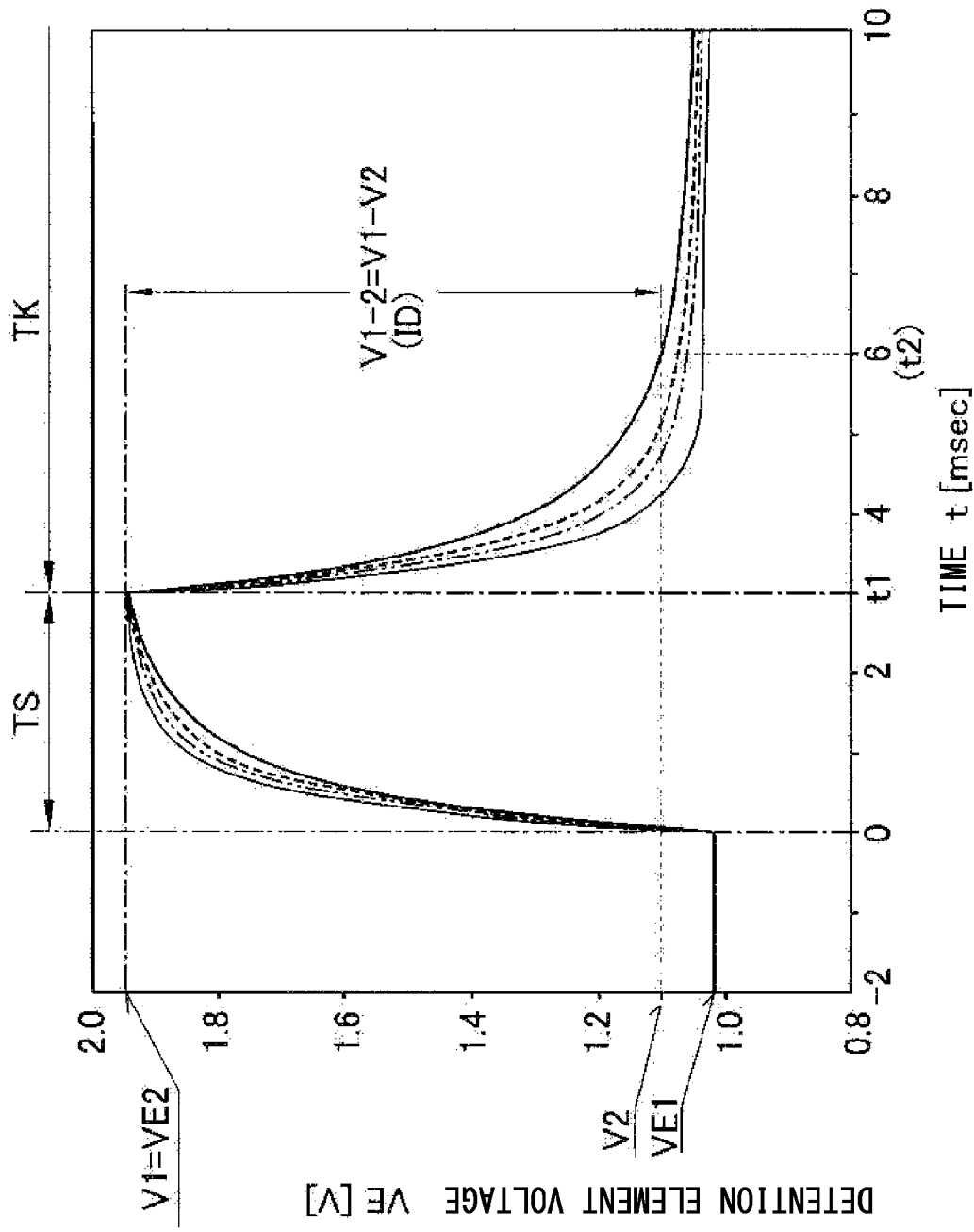
FIG. 2 is a chart showing a change in detection element voltage when a voltage shift is performed for a detection element by the oxygen sensor control apparatus according to the embodiment.

The period in which the transistor Tr2 is turned on for the voltage shift from the pre-shift voltage VE1 to the post-shift voltage VE2 will be referred to as a voltage shift period TS (see FIG. 2). In this voltage shift period TS, a current flows through the internal resistor (internal resistance Ri), and a charge is accumulated in the internal capacitor (internal capacitance Ci) of the detection element 3 in accordance with a time constant Ci·Ri.

After that, the transistor Tr2 is turned off so as to end the voltage shift period TS. Thus, the flow of external current to the detection element 3 (between its electrodes 3P and 3N) stops, and application of the external voltage stops. As a result, the charge accumulated in the internal capacitor (internal capacitance Ci) self-discharges through the internal resistor (internal resistance Ri). Consequently, the detection element voltage VE decreases exponentially, over the recovery period TK, at a rate corresponding to a time constant substantially determined by the internal resistance Ri and the internal capacitance Ci of the detection element 3, whereby a voltage change from the post-shift voltage VE2 back to the pre-shift voltage VE1 is produced.

When the detection element 3 deteriorates, the impedance of the detection element 3 tends to increase. Therefore, the internal resistance Ri of the detection element at the same temperature (at a given temperature) increases, and the internal capacitance Ci also changes. Therefore, the way (trend) of the above-described exponential voltage change differs (varies) among varying degrees of deterioration. Also, this voltage change is hardly affected by disturbances, and is mainly determined by the impedance (the internal resistance Ri and the internal capacitance Ci) of the detection element 3. Accordingly, a deterioration index ID (described below) which represents the degree of deterioration of the detection element 3 can be detected on the basis of this voltage change.

Notably, as described above, when the oxygen concentration (the concentration of a specific gas) is to be detected, the oxygen sensor 2 is used in a state in which the temperature of the detection element 3 is increased to an activation temperature (for example, about 700° C. as mentioned above) higher than 600° C. in order to cause the detection element 3 to sufficiently function as an oxygen concentration cell. When the temperature of the detection element 3 is about 700° C., the internal resistance Ri of the detection element 3 is very small (100 Ω or less). In the present embodiment, since the resistance of the resistor R4 is 8.25 kΩ, which is far larger than the internal resistance Ri of the detection element 3, the internal resistance voltage Vi (shift voltage VS) generated by the internal resistor (internal resistance Ri) when the transistor Tr2 is turned on assumes a small value. Therefore, the voltage change produced in the recovery period TK is also small, and it is difficult to accurately detect the above-mentioned deterioration index ID.

Although the temperature of the detection element 3 must be maintained at a considerably high temperature (for example, 700° C.) at the time of detection of the oxygen concentration, the temperature of the detection element 3 need not be maintained at such a high temperature when the deterioration index ID is detected. The solid electrolyte body constituting the detection element 3 begins to exhibit oxygen ion conductivity at about 400° C. Also, at the same time, the internal resistance Ri of the detection element 3 becomes sufficiently lower than a value representing an insulating state and becomes sufficiently higher than that in the above-mentioned activated state (for example, at 700° C.). For example, in the present embodiment, when the element temperature is 400° C., the internal resistance Ri of the detection element 3 becomes about 2560 Ω, which is several tens of times that at 700° C. and about one third that of the resistor R4. Accordingly, if the deterioration index ID is detected in this state, the shift voltage VS proportional to the internal resistance Ri can be increased, and the voltage change produced in the recovery period TK can be increased.

In view of the above, in the present embodiment, the deterioration index ID is detected in a state in which the internal resistance Ri of the detection element is larger than the internal resistance Ri (first internal resistance Ri1) at the time when the concentration of the specific gas is detected (in a period during which the concentration of the specific gas can be detected). Specifically, the deterioration index ID is detected when the element temperature is about 400° C. and the internal resistance Ri is 2560 Ω. More specifically, after operation of a vehicle has ended (namely, when detection of the oxygen concentration by the oxygen sensor 2 in which the detection element 3 is activated ends), the supply of electric current to the heater 4 of the oxygen sensor 2 stops simultaneously with the vehicle engine, and a wait time of 10 minutes is allowed to elapse (i.e., until the detection element 3 cools). After that, the supply of electric current to the heater 4 is again controlled with the target resistance set such that the internal resistance Ri becomes 2560 Ω. After the internal resistance Ri becomes 2560 Ω, the deterioration index ID is detected.

FIG. 2 shows changes in the detection element voltage VE during the voltage shift period TS and the recovery period TK at the time when the voltage of the detection element 3 is shifted, for detection of the deterioration index ID, by the oxygen sensor control circuit 1 of the present embodiment. Notably, for detection of the deterioration index ID, the supply of electric current to the heater 4 is controlled such that the internal resistance Ri of the detection element 3 becomes 2560 Ω.

In FIG. 2, before the voltage is shifted (before time t=0), the transistor Tr2 of the voltage shift circuit 19 is off, and the detection element voltage VE is 1.02 V. This detection element voltage VE represents the electromotive force EV of the detection element 3 when the element temperature is about 400° C. This is used as the pre-shift voltage VE1 (=EV).

After that, at time t=0, the voltage shift is started by turning on the transistor Tr2 of the voltage shift circuit 19 (start of the voltage shift period TS). As a result, a current flows through the detection element 3, and a voltage drop is produced across the internal resistor (internal resistance Ri) of the detection element 3. In addition, the detection element voltage VE rises while the internal capacitor (internal capacitance Ci) accumulates a charge. In the present embodiment, the voltage shift period TS is set to 3 msec. At a first detection timing t1 (time t=t1), which is in an end portion (at the end) of the voltage shift period TS, the detection element voltage VE approaches a substantially equilibrated state and becomes the post-shift voltage VE2. In view of the above, the detection element voltage VE is detected at the first detection timing t1, and is used as a first voltage V1 (=the post-shift voltage VE2).

When the voltage shift period TS (3 msec in the present embodiment) is made sufficiently longer than (for example, three times or more) the time constant Ci·Ri under the condition that the internal resistance Ri is controlled such that it becomes a fixed value (Ri=2560Ω in the present embodiment), the post-shift voltage VE2 (first voltage V1) converges to a value which is determined by the internal resistance Ri and which does not change irrespective of the degree of deterioration. Also, at time t=t1, the shift voltage VS, which is the difference (VE2−VE1) between the post-shift voltage VE2 and the pre-shift voltage VE1, becomes equal to the internal voltage Vi proceeds from the internal resistor (internal resistance Ri). Therefore, the post-shift voltage VE2 becomes equal to the sum of the electromotive force EV and the internal voltage Vi (the shift voltage VS) (the post-shift voltage VE2=electromotive force EV+the internal voltage Vi).

When the voltage shift period TS is ended by turning the transistor Tr2 off, the recovery period TK begins. In this recovery period TK, the detection element voltage VE is returned from the post-shift voltage VE2 to the pre-shift voltage VE1. Since the transistor Tr2 is off during this recovery period TK, as is understood from FIG. 1, the charge accumulated in the internal capacitor (the internal capacitance Ci) on account of the shift voltage VS self-discharges through the internal resistor (internal resistance Ri). As a result, the voltage between the electrodes 3P and 3N of the detection element 3 decreases exponentially at a rate corresponding to the time constant substantially determined by the internal resistance Ri and the internal capacitance Ci of the detection element 3, whereby a voltage change from the post-shift voltage VE2 back to the pre-shift voltage VE1 is produced (see FIG. 2). In the present embodiment, the detection element voltage VE is detected at a second detection timing t2 (time t=t2), which is a timing within the recovery period TK and is 3 msec after the end of the voltage shift period TS, and is used as a second voltage V2.

As described above, the supply of electric current to the heater 4 is controlled such that the internal resistance Ri of the detection element 3 becomes 2560 Ω. Therefore, the post-shift voltage VE2 (the first voltage V1) assumes the same or fixed value irrespective of the degree of deterioration. The voltage change produced in the recovery period TK changes depending on the degree of deterioration; i.e., the greater the degree of deterioration, the slower the rate of the decrease in voltage, and the greater the second voltage V2. Namely, the 1-2 voltage difference V1-2 (=V1−V2), which is the difference between the first voltage V1 and the second voltage V2, changes depending on the degree of deterioration; i.e., the greater the degree of deterioration, the smaller the value of the 1-2 voltage difference V1-2 (=V1−V2). Accordingly, this 1-2 voltage difference V1-2 can be used as a deterioration index ID which indicates the degree of deterioration of the detection element 3.

Notably, in the present embodiment, the 1-2 voltage difference V1-2 (the deterioration index ID) at the time when the internal resistance Ri is 2560Ω (the element temperature is about 400° C.) is detected. However, the value of the internal resistance Ri at the time of detection of the deterioration index ID (1-2 voltage difference V1-2) may be freely determined within a range in which a difference in the degree of deterioration of the detection element 3 can be distinguished as a difference in the deterioration index ID (1-2 voltage difference V1-2).

Next, control of the oxygen sensor control circuit 1 according to the present embodiment, in particular, operation of the microprocessor 10, will be described with reference to the flowchart of FIG. 3.

Figure 3:
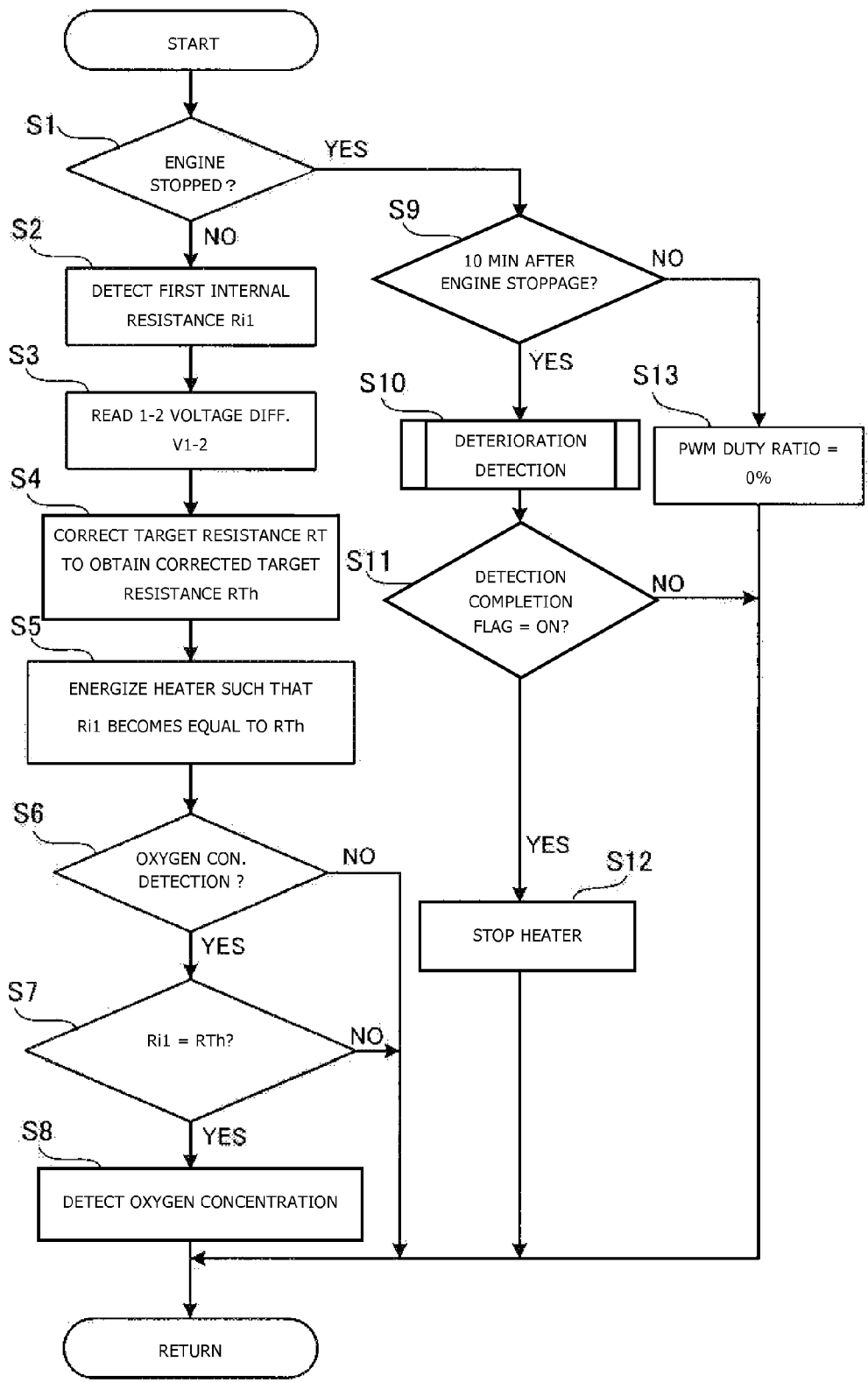
FIG. 3 is a flowchart showing the processing operation of a microcomputer of the oxygen sensor control apparatus according to the embodiment.

The control program shown in FIG. 3 is repeatedly called, as one of programs to be executed by the microprocessor 10, every time the output of the PWM output port 18 for controlling the supply of electric current to the heater 4 is updated (namely, at constant intervals). Also, a necessary initial setting is performed separately before this program is called, whereby the output of the I/O output port 16 is brought to the L level. Therefore, the potential at the node T, which is the output of the pulse signal output circuit 11, becomes +5 V, and the transistor Tr2 is turned off.

First, in step S1, the microprocessor 10 determines whether or not the engine is stopped. In the case where the engine is not stopped (NO; that is, the engine is being operated), the microprocessor 10 proceeds to step S2. After that point in time, the microprocessor 10 detects the first internal resistance Ri1, which is the internal resistance Ri of the detection element 3 when the oxygen concentration is detected (a period during which the oxygen concentration can be detected), outputs a PWM duty ratio for heater energization control, and detects the oxygen concentration. First, in step S2, the microprocessor 10 detects the first internal resistance Ri1.

Subsequently, in step S3, the microprocessor 10 reads out the 1-2 voltage difference V1-2 (see FIG. 6: step S1078), which was detected after the previous operation of the engine as a deterioration index ID by a deterioration detection processing routine described below, and which was stored in a non-volatile memory (not illustrated).

Next, in step S4, the microprocessor 10 corrects a target resistance RT in accordance with the value of the 1-2 voltage difference V1-2 (the deterioration index ID) to thereby obtain a corrected target resistance RTh. In order to maintain the temperature of the detection element 3 at 700° C., the correction is performed such that the smaller the value of the 1-2 voltage difference V1-2 (the greater the degree of deterioration), the larger the value of the corrected target resistance RTh. This is because the first internal resistance Ri1 at the same temperature increases with the degree of deterioration of the detection element 3. Therefore, in order to maintain the element temperature at a fixed temperature, it is necessary to increase the corrected target resistance RTh with an increase in the first internal resistance Ri1.

Next, in step S5, the microprocessor 10 controls the supply of electric current to the heater 4 through use of the corrected target resistance RTh and the first internal resistance Ri1 such that the first internal resistance Ri1 becomes equal to the corrected target resistance RTh. Specifically, by means of PID control or PI control, the microprocessor 10 determines a PWM duty ratio for controlling the supply of electric current to the heater 4, and outputs a PWM pulse from the PWM output port 18. As a result, the heater 4 is PWM-controlled, whereby the temperature of the detection element 3 is controlled and maintained at 700° C. irrespective of the degree of deterioration of the detection element 3.

Next, in step S6, the microprocessor 10 determines whether or not oxygen concentration detection timing has come to pass. In the present embodiment, the oxygen concentration is detected every time the PWM duty ratio for heater energization control is updated 10 times by the processing of steps S2 to S5. In step S6, the microprocessor 10 determines whether or not the present timing is the timing for detecting the oxygen concentration. In the case where the present timing is not the timing for detecting the oxygen concentration (NO), the microprocessor 10 ends the processing. In the case where the present timing is the timing for detecting the oxygen concentration (YES), the microprocessor 10 proceeds to step S7.

In step S7, the microprocessor 10 determines whether or not the first internal resistance Ri1 is equal to the corrected target resistance RTh. When the oxygen concentration is detected, the detection element 3 must be heated to a predetermined activation temperature (700° C. in the present embodiment) (namely, the first internal resistance Ri must be equal to the corrected target resistance RTh). Therefore, before detecting the oxygen concentration, the microprocessor 10 determines in step S7 whether or not such a condition is satisfied. In the case where the microprocessor 10 determines in step S7 that the first internal resistance Ri1 is not equal to the corrected target resistance RTh (NO), the microprocessor 10 ends the processing. Meanwhile, in the case where the first internal resistance Ri1 is equal to the corrected target resistance RTh (YES), the microprocessor 10 proceeds to step S8. After detecting the oxygen concentration in step S8, the microprocessor 10 ends the processing.

Meanwhile, in the case where the microprocessor 10 determines in step S1 that the engine is stopped (YES), the microprocessor 10 proceeds to step S9. In step S9, the microprocessor 10 determines whether or not 10 min has elapsed after the engine has been stopped. In the case where 10 min has not yet elapsed (NO), the microprocessor 10 proceeds to step S13 so as to set the PWM duty ratio for heater energization control to 0% and output the duty ratio from the PWM output port 18. After that, the microprocessor 10 ends the processing. As a result, no electric current is supplied to the heater 4 during the 10 min period after the engine is stopped. Therefore, the temperature of the detection element 3 decreases gradually.

When a time of 10 min has elapsed after the engine has been stopped, the microprocessor 10 makes a YES determination in step S9, and proceeds to step S10 so as to execute a deterioration detection processing routine. After completing this deterioration detection processing routine (step S10), the microprocessor 10 proceeds to step S11. In the case where the microprocessor 10 determines in the step S11 that a detection completion flag described below (see FIG. 4: step S108) is off (that is, the detection of the deterioration index ID has not yet been completed) (NO), the microprocessor 10 ends the processing. Meanwhile, in the case where the microprocessor 10 determines that the detection completion flag is on (that is, the detection of the deterioration index ID has been completed) (YES), the microprocessor 10 proceeds to step S12 so as to completely stop the supply of electric current to the heater 4. After that, the microprocessor 10 ends the processing.

The above-described program (the series of processing steps) is called at constant intervals, and is executed from step S1. However, after the engine is stopped and the detection completion flag is turned on so as to end this processing, the calling of this program is stopped until the engine is started once again.

Next, the deterioration detection processing routine shown in step S10 will be described with reference to the flowchart of FIG. 4.

First, in step S101, the microprocessor 10 executes a voltage shift subroutine (described in detail below). In this voltage shift subroutine, the microprocessor 10 shifts the detection element voltage VE, and obtains the pre-shift voltage VE1, the post-shift voltage VE2, and the shift voltage VS. Also, when the voltage shift subroutine is ended, the output of the I/O output port 16 is brought to the H level. Therefore, the potential of the node T (the output of the pulse signal output circuit 11) becomes 0 V, and the transistor Tr2 is turned on.

Next, the microprocessor 10 proceeds to step S102 so as to return the output of the I/O output port 16 to the L level. As a result, the potential of the node T (the output of the pulse signal output circuit 11) becomes +5 V, and the transistor Tr2 is turned off.

Next, the microprocessor 10 proceeds to step S103 so as to calculate the internal resistance Ri from the pre-shift voltage VE1 (the electromotive force EV) and the shift voltage VS (the internal voltage Vi) obtained in the voltage shift subroutine (step S101). In step S104 subsequent thereto, the microprocessor 10 controls the supply of electric current to the heater 4 such that the internal resistance Ri thus obtained becomes equal to a second target resistance RU (RU=2560 Ω in the present embodiment). Specifically, through PID control or PI control, the microprocessor 10 determines a PWM duty ratio for controlling the supply of electric current to the heater 4, and outputs a PWM pulse from the PWM output port 18. As a result, the heater 4 is PWM-controlled, whereby the temperature of the detection element 3 is controlled to about 400° C.

Next, in step S105, the microprocessor 10 determines whether or not deterioration index detection timing has come to pass. In step S106 subsequent thereto, before detecting the deterioration index ID, the microprocessor 10 determines whether or not the internal resistance Ri thus obtained is equal to the second target resistance RU (=2560Ω). In the present embodiment, the microprocessor 10 performs the determination of step S105 every time the PWM duty ratio for heater energization control is updated 10 times by the processing of steps S101 to S104. In the case where the present timing is not the deterioration index detection timing (NO), the microprocessor 10 ends the processing. In the case where the present timing is the deterioration index detection timing (YES), the microprocessor 10 proceeds to step S106 in order to determine whether or not the internal resistance Ri is equal to the second target resistance RU. In the case where the microprocessor 10 determines in step S106 that the internal resistance Ri is not equal to the second target resistance RU (NO), the microprocessor 10 ends the processing.

Meanwhile, in the case where the microprocessor 10 determines in step S106 that the internal resistance Ri is equal to the second target resistance RU (YES), the microprocessor 10 proceeds to step S107 so as to execute a deterioration index detection subroutine for detecting the deterioration index ID (the details of the subroutine are described below). After completing the deterioration index detection subroutine, in step S108, the microprocessor 10 turns on a detection completion flag which indicates that the detection of the deterioration index ID has been completed. After that, the microprocessor 10 ends this deterioration detection processing routine.

Figure 5:
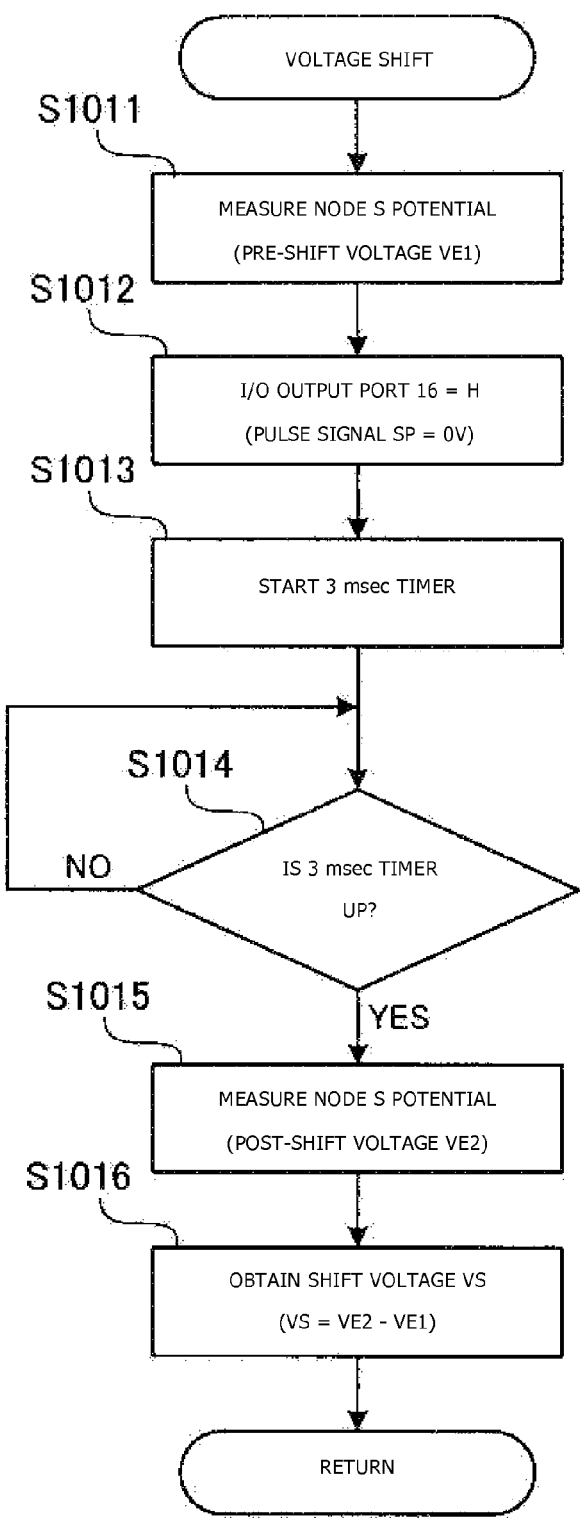
FIG. 5 is a flowchart showing the details of a voltage shift subroutine.

Next, the voltage shift subroutine of step S101 will be described with reference to the flowchart of FIG. 5. In this voltage shift subroutine, as described above, the microprocessor 10 shifts the detection element voltage VE by means of the voltage shift circuit 19, and obtains the pre-shift voltage VE1, the post-shift voltage VE2, and the shift voltage VS.

First, in step S1011, the microprocessor 10 obtains the output of the output detection circuit 12 via the A/D input port 17, and measures the potential at the node S. Namely, the microprocessor 10 measures the potential (the pre-shift voltage VE1) at the node Q via the low-pass filter circuit 15, before the voltage shift, which is described next. At that time, the output of the I/O output port 16 is brought to the L level, whereby the potential at the node T (the output of the pulse signal output circuit 11) becomes +5 V, and the transistor Tr2 is turned off. Therefore, no current flows through the resistor R4, and the potential at the node Q (and the node S) becomes equal to the electromotive force EV of the detection element 3. Accordingly, the potential (the pre-shift voltage VE1) at the node Q (and the node S) measured in this step S1011 is equal to the value of the electromotive force EV (VE1=EV).

Next, the microprocessor 10 proceeds to step S1012, and brings the output of the I/O output port 16 to the H level. As a result, the potential at the node T (the output of the pulse signal output circuit 11) becomes 0 V, and the transistor Tr2 is turned on. Notably, this timing corresponds to the time t=0 in FIG. 2. Subsequently, the microprocessor 10 proceeds to step S1013 so as to start a timer for clocking the time of 3 msec.

When the transistor Tr2 is turned on, a current I flows through the resistor R4, and this current I flows into the detection element 3. As a result, due to this current I, a voltage drop is produced across the internal resistor (internal resistance Ri), and a charge is gradually accumulated by the internal capacitor (internal capacitance Ci). Therefore, the potential at the node Q begins to increase from the electromotive force EV with the progress of accumulation of charge by the internal capacitor (internal capacitance Ci). The voltage which is superimposed on the electromotive force EV at the node Q is the voltage produced across the internal resistor (internal resistance Ri) and the internal capacitor (internal capacitance Ci).

In step S1014 subsequent thereto, the microprocessor 10 determines whether or not the 3 msec timer started in step S1013 is up. Namely, in the case where the timer is not up (NO), the microprocessor 10 repeats the determination of step S1014. Accordingly, during this period, the accumulation of the charge by the internal capacitor (internal capacitance Ci) proceeds, and the potential at the node Q increases and approaches an equilibrium state. When 3 msec has elapsed and the timer is up (YES), the microprocessor 10 proceeds to step S1015.

In step S1015, at the first detection timing t1 (time t=t1=3 msec; see FIG. 2) (when 3 msec has elapsed after the transistor Tr2 has been turned on), the microprocessor 10 again obtains the output of the output detection circuit 12 via the A/D input port 17, and measures the potential at the node S. Namely, the microprocessor 10 measures the potential at the node Q via the low-pass filter circuit 15. The potential at the node Q, which begins to rise when the time t=0, has generally reached the equilibrium state during the 3 msec period (the voltage shift period TS) (see FIG. 2), and the value at the time t=t1, which was measured in the step S1015, is used as the post-shift voltage VE2.

Next, the microprocessor 10 proceeds to step S1016 so as to obtain the shift voltage VS by calculating the difference (VE2−VE1) between the post-shift voltage VE2 and the pre-shift voltage VE1, which have already been obtained, and ends the voltage shift subroutine.

Figure 6:
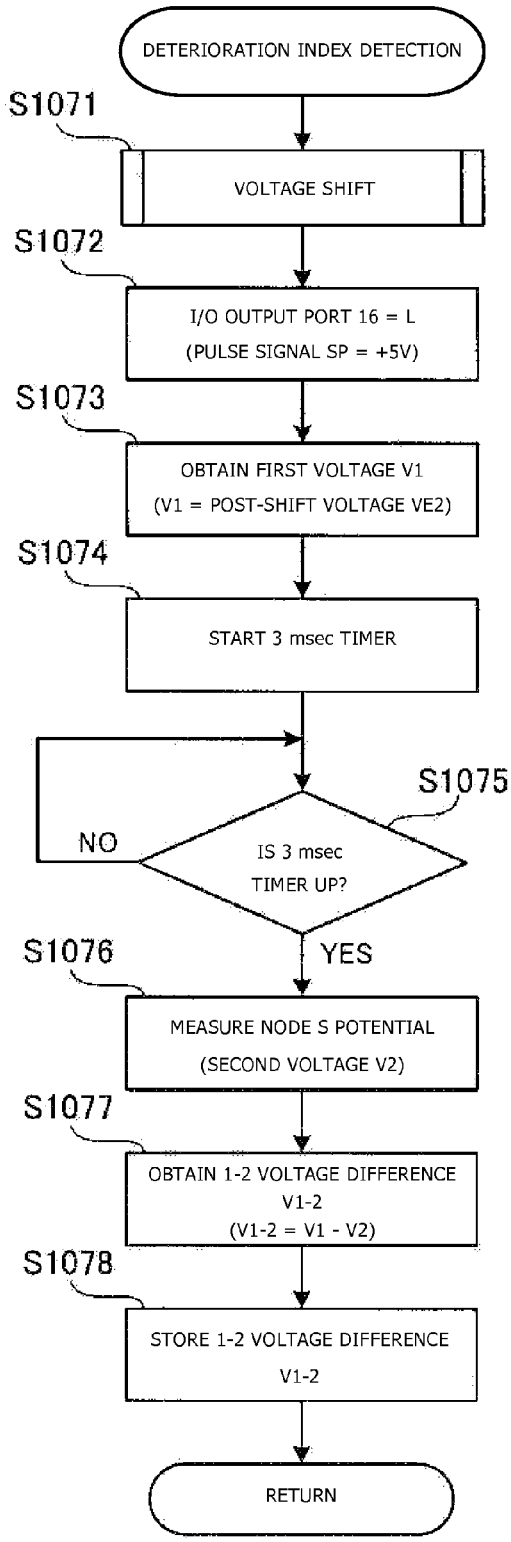
FIG. 6 is a flowchart showing the details of a deterioration index detection subroutine.

Next, the deterioration index detection subroutine of step S107 will be described with reference to the flowchart of FIG. 6. Notably, as described above, the microprocessor 10 executes the deterioration index detection subroutine (step S107) when the microprocessor 10 determines in step S106 that the internal resistance Ri of the detection element 3 is equal to the second target internal resistance RU (=2560 Ω) (Yes).

First, in step S1071, the microprocessor 10 executes the same voltage shift subroutine as that executed in step S101 of the deterioration detection processing routine (step S10). At the end of the voltage shift subroutine (at the end of step S1016), the output of the I/O output port 16 is brought to the H level. Therefore, the potential of the node T (the output of the pulse signal output circuit 11) becomes 0 V, and the transistor Tr2 is turned on.

Next, the microprocessor 10 proceeds to step S1072 so as to return the output of the I/O output port 16 to the L level. As a result, the potential of the node T (the output of the pulse signal output circuit 11) becomes +5 V, and the transistor Tr2 is turned off. With this operation, the voltage shift period TS ends, and the recovery period TK starts subsequently.

In step S1073 subsequent thereto, the microprocessor 10 obtains (copies), as the first voltage V1, the post-shift voltage VE2 obtained in step S1015 of the voltage shift subroutine (at the first detection timing t1) (V1=VE2).

Subsequently, the microprocessor 10 proceeds to step S1074 so as to start a timer for clocking the time of 3 msec.

Since the transistor Tr2 is turned off, no external voltage is applied to the detection element 3 via the +5 V power, and no current flows through the detection element 3. Therefore, in the detection element 3, the charge accumulated by the internal capacitor (internal capacitance Ci) self-discharges through the internal resistor (internal resistance Ri). As a result, the potential at the node Q decreases exponentially at a rate corresponding to the time constant substantially determined by the internal resistance Ri and the internal capacitance Ci, whereby a voltage change from the post-shift voltage VE2 to the pre-shift voltage VE1 is produced.

In step S1075 subsequent thereto, the microprocessor 10 determines whether or not the 3 msec timer started in step S1074 is up. Namely, in the case where the timer is not up (NO), the microprocessor 10 repeats the determination of step S1075. When 3 msec has elapsed and the timer is up (YES), the microprocessor 10 proceeds to step S1076.

In step S1076, at the second detection timing t2 (time t=t2=6 msec; see FIG. 2) (when 3 msec has elapsed after the transistor Tr2 was turned off), the microprocessor 10 again obtains the output of the output detection circuit 12 via the A/D input port 17, and measures the potential at the node S. Namely, the microprocessor 10 measures the potential at the node Q via the low-pass filter circuit 15. The value at the time t=t2, which was measured in this step S1076, is used as the second voltage V2.

Next, the microprocessor 10 proceeds to step S1077, and obtains the 1-2 voltage difference V1-2, which is the deterioration index ID, by calculating the difference (V1−V2) between the first voltage V1 and the second voltage V2, which have already been obtained.

Moreover, the microprocessor 10 proceeds to step S1078 so as to store the obtained 1-2 voltage difference V1-2 in the non-volatile memory, and ends the present deterioration index detection subroutine.

Notably, in the present embodiment, the pulse signal output circuit 11, the voltage shift circuit 19, the low-pass filter circuit 15, the output detection circuit 12, and the microprocessor 10 which executes steps S101 to S103 correspond to the resistance index detection means; and the internal resistance Ri detected by the circuits and the microprocessor corresponds to the resistance index IR. The pulse signal output circuit 11, the voltage shift circuit 19, and the microprocessor 10 which executes step S1071 correspond to the voltage shift means. The pulse signal output circuit 11, the voltage shift circuit 19, and the microprocessor 10 which executes step S1072 correspond to the recovery means.

The resistance index detection means and the voltage shift means share the pulse signal output circuit 11 and the voltage shift circuit 19 used for the voltage shift. In the present embodiment, the resistance index detection means and the voltage shift means share the voltage shift subroutine (step S101, S1071), and the resistance index detection means performs the 3 m sec voltage shift in the same manner as in the voltage shift period TS in which the voltage shift means performs the voltage shift. However, the period of voltage shift in which the resistance index detection means detects the resistance index IR may differ from the voltage shift period TS in which the voltage shift means performs the voltage shift so as to detect the deterioration index ID; and the resistance index detection means and the voltage shift means may perform different subroutines for such a voltage shift. The voltage shift means, which turns on the transistor Tr2 of the voltage shift circuit 19, and the recovery means, which turns off the transistor Tr2, use the same circuits (the pulse signal output circuit 11 and the voltage shift circuit 19).

The microprocessor 10 which executes steps S106 and S107 corresponds to the deterioration index detection means, and detects the 1-2 voltage difference V1-2, which is the deterioration index ID, when the internal resistance Ri is equal to the second target resistance RU (=2560 Ω). The second target resistance RU (=2560 Ω) corresponds to the detection permission value IP.

The microprocessor 10 which executes step S2 corresponds to the first internal resistance detection means; and the microprocessor 10 which executes step S4 corresponds to the target resistance correction means.

The heater control circuit 13 and the microprocessor 10 which executes step S5 correspond to the first heater energization control means; and the heater control circuit 13 and the microprocessor 10 which executes step S104 correspond to the second heater energization control means.

As described above, the oxygen sensor control circuit 1 of the present embodiment comprises voltage shift means (see FIG. 6: step S1071) for shifting the detection element voltage VE from the pre-shift voltage VE1 to the post-shift voltage VE2; and recovery means (see FIG. 6: step S1072) for returning the detection element voltage VE from the post-shift voltage VE2 to the pre-shift voltage VE1. The recovery means is effected after the end of the voltage shift period TS in which the detection element voltage VE is shifted by the voltage shift means, and is carried out by self-discharge through the internal resistance Ri and the internal capacitance Ci of the detection element 3. The oxygen sensor control circuit 1 further comprises deterioration index detection means (see FIG. 4: step S107) for detecting the deterioration index ID (1-2 voltage difference V1-2) of the detection element 3 on the basis of the voltage change in the detection element voltage VE produced in the recovery period TK in which the detection element voltage VE is returned to the pre-shift voltage VE1 by the recovery means. In the recovery period TK, the voltage between the electrodes 3P and 3N of the detection element 3 decreases exponentially at a rate corresponding to the time constant generally determined by the internal resistance Ri and the internal capacitance Ci of the detection element 3, whereby a voltage change from the post-shift voltage VE2 back to the pre-shift voltage VE1 is produced. Moreover, when the detection element 3 deteriorates, the impedance of the detection element 3 tends to increase, and the internal resistance Ri at the same temperature increases. In addition, the internal capacitance Ci also changes. Therefore, the way that the above-described exponential voltage change varies differs depending on the degree of deterioration. Also, the difference in this voltage change is hardly affected by external disturbances, and is generally determined by the impedance of the detection element 3. Accordingly, the oxygen sensor control circuit 1 of the present embodiment which detects the deterioration index on the basis of this voltage change can accurately detect the degree of deterioration of the detection element 3 of the oxygen sensor 2.

In addition to the first internal resistance detection means (see FIG. 3: step S2) and the first heater energization control means (step S5), the oxygen sensor control circuit 1 of the present embodiment comprises target resistance correction means (step S4) for correcting a target resistance RT used in feedback control in accordance with the deterioration index ID (1-2 voltage difference V1-2) detected by the deterioration index detection means, to thereby obtain the corrected target resistance RTh. By virtue of this configuration, the supply of electric current to the heater 4 can be properly feedback-controlled by changing the target resistance RT in accordance with the degree of deterioration of the detection element 3. Therefore, the element temperature can be maintained at a proper activation temperature. In addition, acceleration of the deterioration by an increase in the element temperature can be prevented.

The oxygen sensor control circuit 1 of the present embodiment further comprises resistance index detection means (see FIG. 4: steps S101 to S103) for detecting the internal resistance Ri (resistance index IR) before detection of the deterioration index ID (1-2 voltage difference V1-2). The deterioration index detection means (steps S106 and S107) detects the deterioration index ID when the internal resistance Ri (resistance index IR) is equal to the second target resistance RU (=2560 Ω: detection permission value IP) (this state is determined in step S106). By virtue of this configuration, the deterioration index ID can be detected under a constant condition, whereby the deterioration index ID (1-2 voltage difference V1-2) can be detected accurately.

Figure 4:
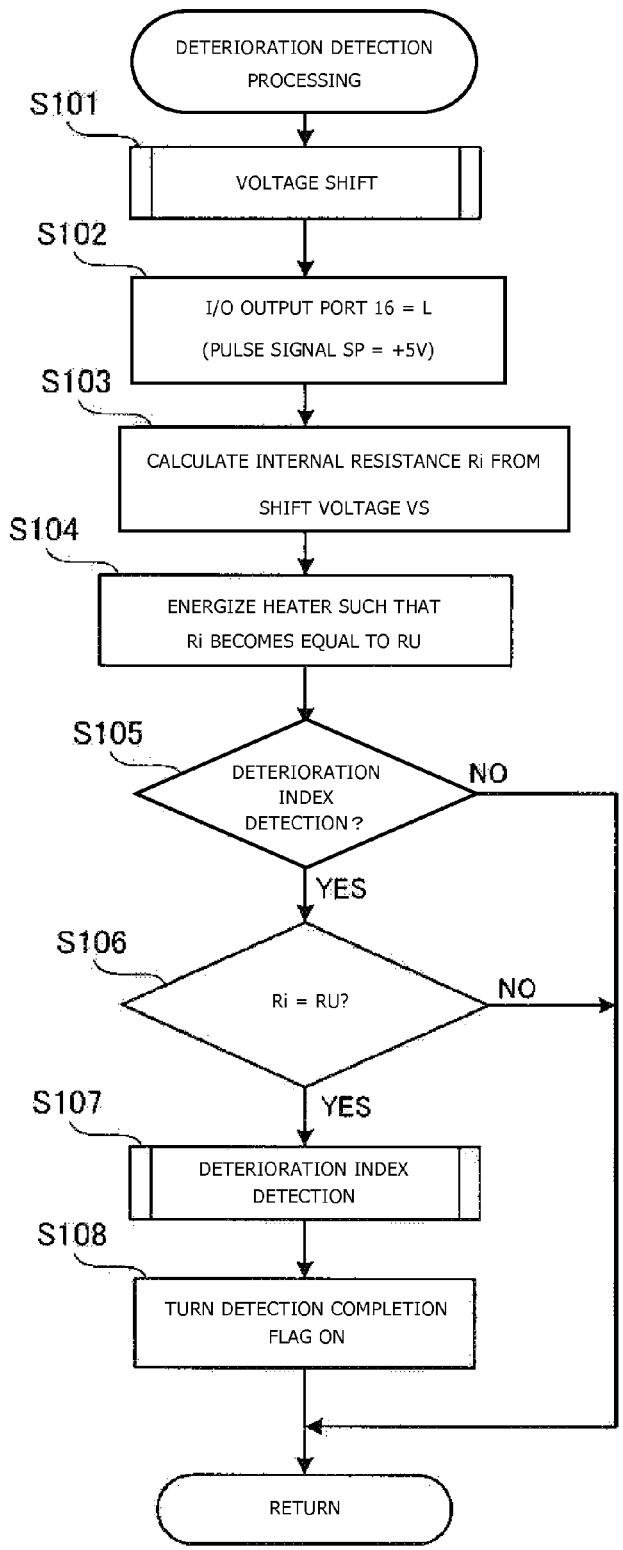
FIG. 4 is a flowchart showing the details of a deterioration detection processing routine.

The oxygen sensor control circuit 1 of the present embodiment feedback-controls the supply of electric current to the heater 4 such that the internal resistance Ri (resistance index IR) becomes equal to the second target resistance RU (detection permission value IP) (second heater energization control means, see FIG. 4: step S104). By virtue of this configuration, the deterioration index ID (1-2 voltage difference V1-2) can be detected reliably at the timing at which the internal resistance Ri (resistance index IR) becomes equal to the second target resistance RU (detection permission value IP).

In the oxygen sensor control circuit 1 of the present embodiment, the 1-2 voltage difference V1-2, which serves as the deterioration index ID, can be readily obtained through a simple operation. That is, when the internal resistance Ri (resistance index IR) is equal to the second target resistance RU (detection permission value IP), two voltages are measured; i.e., the first voltage V1 (=the post-shift voltage VE2) at the first detection timing t1 (see FIG. 5: step S1015) within the voltage shift period TS and the second voltage V2 at the second detection timing t2 (see FIG. 6: step S1076) within the recovery period TK after the voltage shift period TS.

In the oxygen sensor control circuit 1 of the present embodiment, similar to the voltage shift means (see FIG. 6: step S1071), the resistance index detection means (see FIG. 4: steps S101 to S103) shifts the detection element voltage VE from the pre-shift voltage VE1 to the post-shift voltage VE2 (step S101); and the resistance index detection means shares the pulse signal output circuit 11 and the voltage shift circuit 19, used for such a shift operation, with the voltage shift means. Therefore, it is unnecessary to provide separate circuits for the resistance index detection means and the voltage shift means, and the processing apparatus can be made inexpensive and compact.

In the oxygen sensor control circuit 1 of the present embodiment, the deterioration index ID (internal resistance Ri) is detected after 10 minutes or more has elapsed after the engine is stopped; and the deterioration index detection means detects the deterioration index ID in a period in which the internal resistance Ri of the detection element 3 is greater than the first internal resistance Ri1 (100 Ω or less), which is the internal resistance Ri at the time when the concentration of the specific gas (oxygen concentration) is detected; namely, in a period in which the internal resistance Ri is equal to 2560 Ω. By virtue of this configuration, the voltage change in the detection element voltage VE occurring in the recovery period TK becomes large, whereby the deterioration index ID can be detected accurately.

In the above, the gas sensor processing apparatus of the present invention has been described on the basis of the oxygen sensor control circuit 1 of the oxygen sensor 2 of the present embodiment. However, the present invention is not limited to the above-described embodiment, and, needless to say, the present invention may be freely modified in accordance with the application thereof without departing from the scope of the invention.

For example, the "gas sensor" in the present invention is not limited to an oxygen sensor which detects the concentration of oxygen concentration, and may be an NOx sensor for detecting the concentration of nitrogen oxide (NOx), an HC sensor for detecting the concentration of hydro carbon, or the like.

The present invention may be applied to a gas sensor processing apparatus which processes the output of a gas sensor having no heater.

In the present embodiment, the internal resistance Ri is used as the resistance index IR; however, the shift voltage VS corresponding to the internal resistance voltage Vi may be used as the resistance index IR.

In the present embodiment, the above-described 1-2 voltage difference V1-2 is obtained as a deterioration index ID, and the target resistance RT is corrected through use of the deterioration index ID. However, the deterioration index ID is not limited thereto. For example, in the present embodiment, the post-shift voltage VE2 at the time t1 (=3 msec) (V1=VE2) is used as the first voltage V1 in order to obtain the 1-2 voltage difference V1-2. However, the embodiment may be modified such that the detection element voltages VE (VE3, VE4) at predetermined two timings (e.g., times t3 (=3.5 msec) and t4 (=6.5 msec) in FIG. 2) within the recovery period TK are measured, and the difference therebetween is used as the deterioration index ID. Alternatively, the embodiment may be modified such that the detection element voltage VE generated between the electrodes 3P and 3N of the detection element 3 during the recovery period TK is periodically measured, and the time constant of an exponential function which approximates a curve representing the changing detection element voltage VE is obtained as the deterioration index ID.

In the present embodiment, the deterioration index ID is detected when the internal resistance Ri becomes equal to the second target resistance RU (=2560 Ω) corresponding to a detection element temperature of about 400° C. However, the second target resistance RU may be freely determined within the range in which the deterioration index ID can be detected accurately.

In the present embodiment, the length of the voltage shift period TS is set to 3 msec, and the length of the period from the first detection timing t1 to the second detection timing t2 is set to 3 msec. However, the length of these periods may be freely determined within the range in which the deterioration index ID can be detected accurately.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2012-004568 filed Jan. 13, 2012, incorporated herein by reference in its entirety.

What is claimed is:

1. A gas sensor processing apparatus for processing an output of a gas sensor including a detection element which is formed of a solid electrolyte body, which has a pair of electrodes, and which detects the concentration of a specific gas, comprising:
   voltage shift means for shifting a detection element voltage produced between the electrodes of the detection element from a pre-shift voltage to a post-shift voltage different from the pre-shift voltage;
   recovery means for returning the detection element voltage from the post-shift voltage to the pre-shift voltage through self-discharge by an internal capacitor of the detection element after the end of a voltage shift period in which the detection element voltage is shifted by the voltage shift means; and
   deterioration index detection means for detecting a deterioration index representing the degree of deterioration of the detection element on the basis of a change in the detection element voltage in a recovery period in which the detection element voltage is returned to the pre-shift voltage by the recovery means;
   wherein, when the detection element is represented by an equivalent circuit, the detection element is equivalent to a series circuit between the electrodes thereof, the series circuit including a cell that generates an electromotive force in accordance with the concentration of the specific gas and an internal impedance composed of an internal resistor and an internal capacitor connected in parallel, and
   the post-shift voltage is greater than the electromotive force generated by the detection element.

2. The gas sensor processing apparatus as claimed in claim 1, wherein
   the gas sensor includes a heater for heating the detection element; and
   the gas sensor processing apparatus further comprises:
   first internal resistance detection means for detecting a first internal resistance which is an internal resistance of the detection element when the detection element detects the concentration of the gas;
   first heater energization control means for feedback-controlling the supply of electricity to the heater such that the first internal resistance becomes equal to a target resistance; and
   target resistance correction means for correcting the target resistance in accordance with the deterioration index detected by the deterioration index detection means.

3. The gas sensor processing apparatus as claimed in claim 1, further comprising:
   resistance index detection means for detecting a resistance index before the deterioration index detection means detects the deterioration index, the resistance index being the internal resistance of the detection element or an internal voltage proceeds from the internal resistance, wherein
   the deterioration index detection means detects the deterioration index when the resistance index is equal to a predetermined detection permission value.

4. The gas sensor processing apparatus as claimed in claim 2, wherein
   the gas sensor includes a heater for heating the detection element; and
   the gas sensor processing apparatus further comprises:
   second heater energization control means for feedback-controlling the supply of electricity to the heater such that the resistance index detected by the resistance index detection means becomes equal to the detection permission value.

5. The gas sensor processing apparatus as claimed in claim 3, wherein the deterioration index detection means detects, as the deterioration index, a 1-2 voltage difference, which is the difference between a first voltage, which is the detection element voltage at a first detection timing within the voltage shift period, and a second voltage, which is the detection element voltage at a second detection timing within the recovery period following the voltage shift period.

6. The gas sensor processing apparatus as claimed in claim 3, wherein the resistance index detection means and the voltage shift means share a circuit which shifts the detection element voltage of the detection element from the pre-shift voltage to the post-shift voltage.

7. The gas sensor processing apparatus as claimed in claim 1, wherein the deterioration index detection means detects the deterioration index in a period in which the internal resistance of the detection element is greater than a first internal resistance which is the internal resistance at the time when the detection element detects the concentration of the gas.

* * * * *